United States Patent [19]

Sanfilippo

[11] Patent Number: 5,626,135
[45] Date of Patent: May 6, 1997

[54] MEDICAL ELECTRODE

[75] Inventor: Robert M. Sanfilippo, Glendale, Calif.

[73] Assignee: R.S. Supplies, Inc., Fullerton, Calif.

[21] Appl. No.: 420,418

[22] Filed: Apr. 12, 1995

[51] Int. Cl.$^6$ ................................................ A61B 5/0408
[52] U.S. Cl. .......................................... 128/640; 128/641
[58] Field of Search ................................ 128/640, 641; 606/32; 607/149, 152

[56] References Cited

U.S. PATENT DOCUMENTS

| | | | |
|---|---|---|---|
| 4,777,954 | 10/1988 | Keusch et al. | 128/641 |
| 5,042,981 | 8/1991 | Gross | 606/32 |
| 5,133,356 | 7/1992 | Bryan et al. | 128/640 |
| 5,191,887 | 3/1993 | Cartmell | 128/640 |
| 5,197,471 | 3/1993 | Otero | 128/640 |
| 5,225,473 | 7/1993 | Duan | 524/388 |
| 5,309,909 | 5/1994 | Gadsby et al. | 128/640 |
| 5,341,812 | 8/1994 | Allaire et al. | 128/696 |

FOREIGN PATENT DOCUMENTS

| | | | |
|---|---|---|---|
| 9105509 | 5/1991 | WIPO | 128/640 |
| 9300857 | 1/1993 | WIPO | 128/640 |

OTHER PUBLICATIONS

A photograph of a medical electrode manufactured by Sentry Medical Products, Irvine, California.

*Primary Examiner*—Lee S. Cohen
*Attorney, Agent, or Firm*—Knobbe, Martens, Olson & Bear, LLP

[57] ABSTRACT

A medical electrode provides the ability to simultaneously connect at least two medical-electrical monitoring or testing instruments to an electrode positioned at a specific location on a patient's body. The electrode includes a conductive layer with a tab portion extending from a body. The body includes an aperture which is sized and configured to receive a conductive post of the electrode. The tab portion extends outwardly from the body with the aperture receiving the conductive post of the electrode such that the tab portion provides an attachment point for a conventional clip of an auxiliary piece of electrical instrument. The tab portion of the electrode does not interfere with the attachment of an electrical connector of a primary electrical instrument to the conductive post of the electrode.

27 Claims, 5 Drawing Sheets

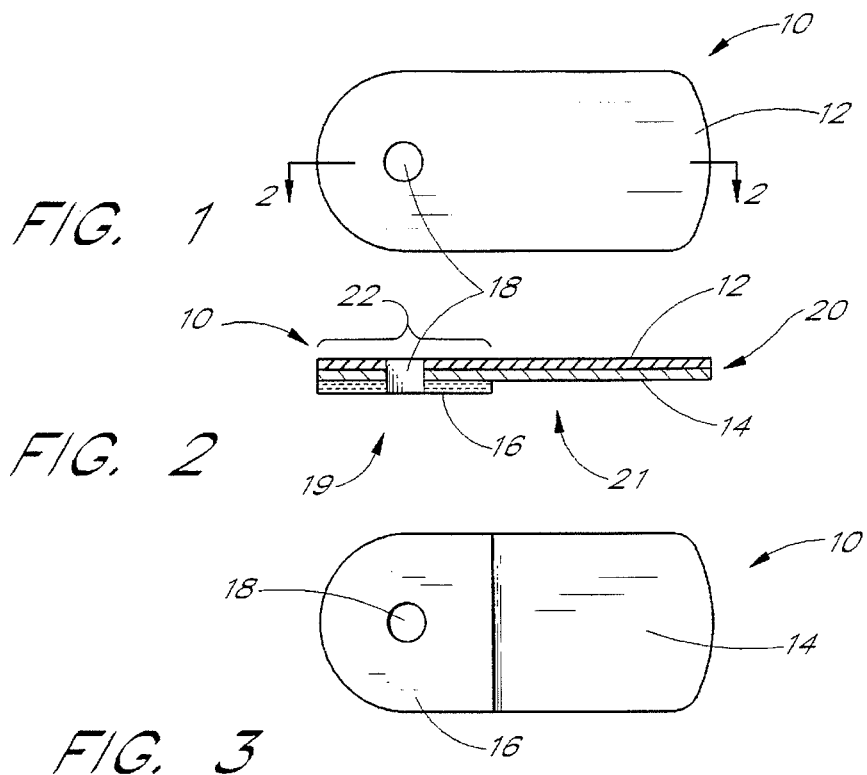
FIG. 1
FIG. 2
FIG. 3
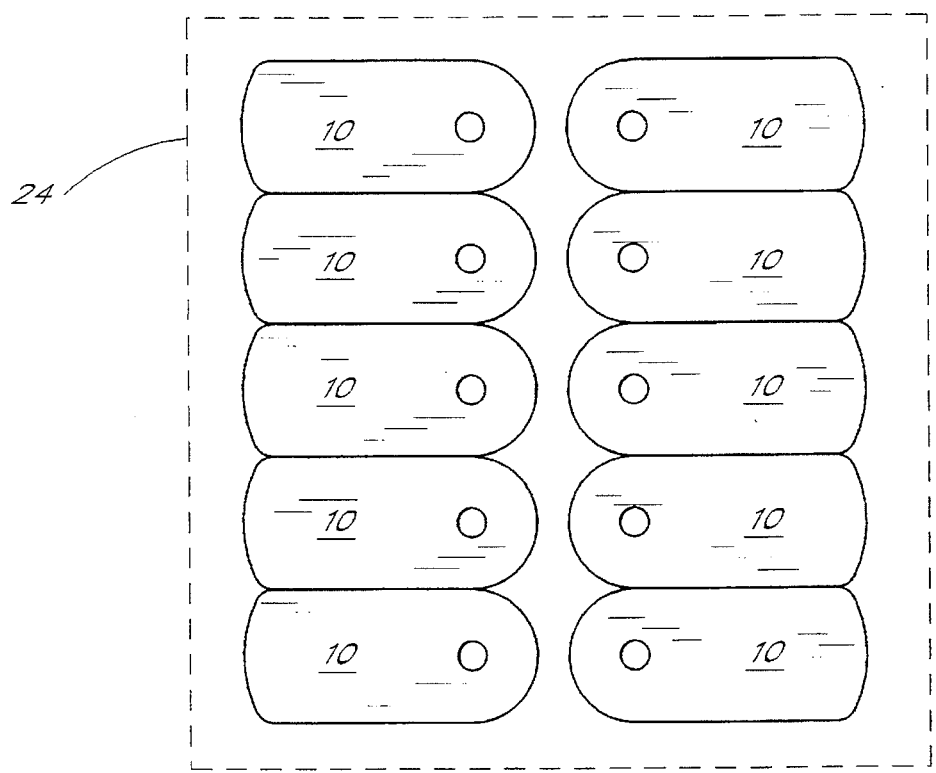
FIG. 4

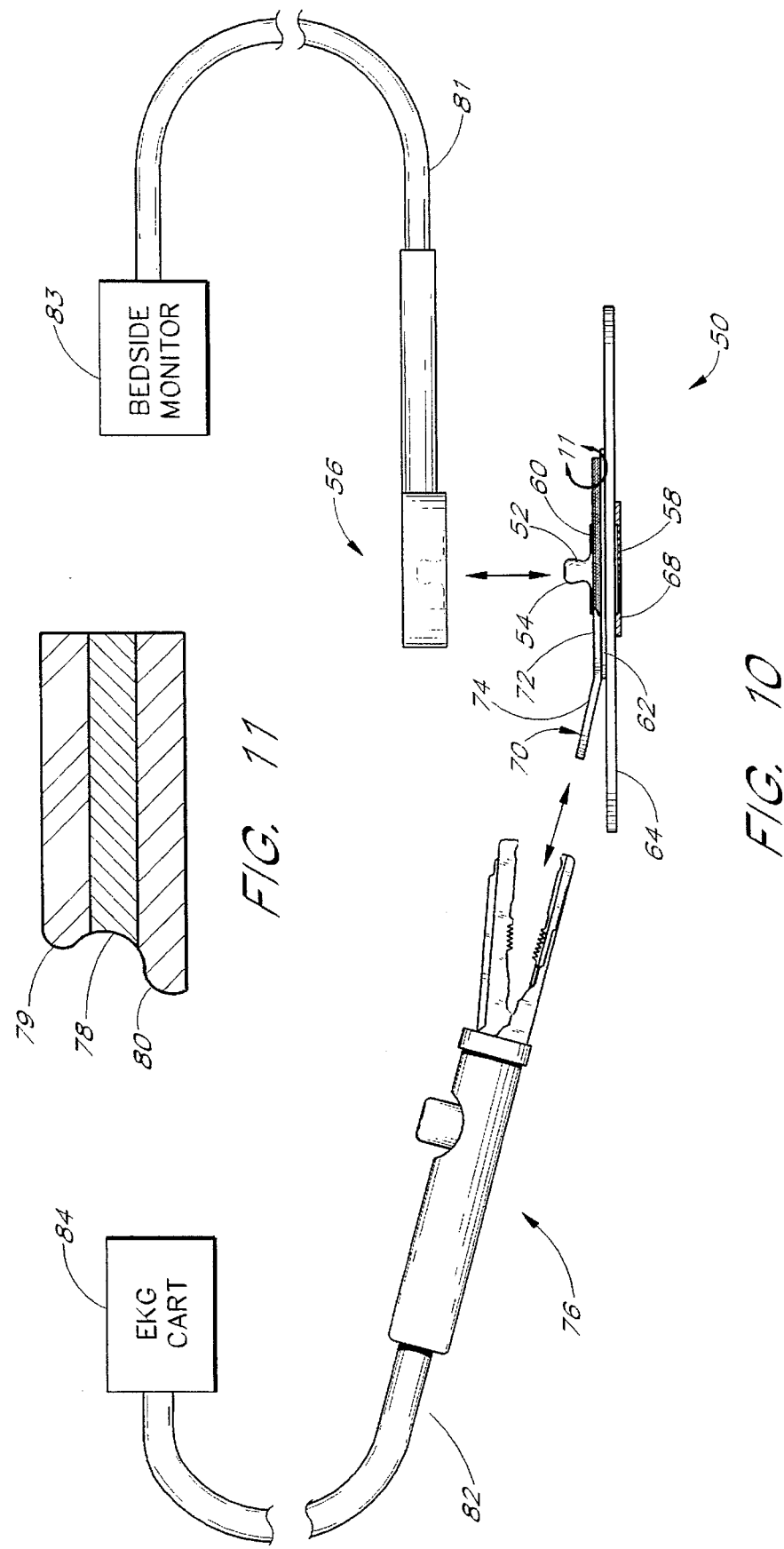

MEDICAL ELECTRODE

BACKGROUND OF THE INVENTION

1. Field of the Invention

The present invention relates in general to a medical device and, in particular, to a medical electrode.

2. Description of the Relevant Art

Medical electrodes are utilized in a number of applications for a variety of diagnostic and monitoring purposes. For instance, electrodes commonly are used to monitor physiological electric potentials to detect muscular activity of a person's heart. The cardiovascular activity of the heart is typically monitored by adhering or connecting electrodes to the skin of the patient at particular locations of interest on the body. The electrodes are then electrically coupled to electrical equipment such as an electrocardiograph (also referred to as EKG) apparatus that monitors the muscular activity of the heart. The resulting traces or output of the EKG provides a diagnostic tool for detecting heart disease and/or heart disfunction of various etiology.

During a conventional cardiovascular examination, the electrodes are affixed directly to the skin of the patient at specific locations. For example, one electrode is generally connected to the chest of the patient, proximate the person's heart. Other electrodes are typically placed on the torso of the patient, near the extremities. It is important to properly locate the electrodes on the patient and position the electrodes without excessive handling. Unnecessary handling of the electrodes increases the tendency of the electrodes to become damaged, thereby destroying or altering the results of the examination.

Two types of electrodes are frequently used to conduct cardiovascular monitoring. The first type of electrode, as known in the art and generally described below, is a snap electrode. The snap electrode includes an electrically conductive post with a male fitting or ball stud integrally connected to one end. Located proximate the ball stud is a flange that extends radially outward from the post. This flange is electrically conductive and is typically integrally connected to the post of the electrode. Integrally attached to the other end of the post, opposite the ball stud, is an electrically conductive component such as a plate for contacting the patient's skin.

A piece of standard medical adhesive tape commonly encircles the post. The post extends through the tape and the tape is attached to the post between the flange and the plate. The surface of the tape coterminous with the plate contains a pressure-sensitive adhesive which is used to connect the electrode to the patient's skin. The tape is often circular or oval in shape, but it will be understood that a wide variety of shapes and types of adhesive tape may be used. As known in the art, the electrode may contain a receptacle or recess located between the plate and the skin of the patient. This recess is typically pre-filled with an electrically conducting material such as a gel to facilitate the electrical connection between the post of the electrode and the patient.

The snap electrode is connected to the electrical equipment by means such as a female coupling that is snap connected to the ball stud. Attached to the female coupling is an electrically conductive wire which connects the electrical device to the monitoring equipment. Thus, the snap electrode provides an electrical path between the patient and the electrical unit.

There are many known types and styles of snap electrodes that are commercially available which have this known structure.

The other type of medical electrode that is commonly used is called a tab electrode. As known, tab electrodes typically include a relatively thin backing material, a conductive layer, and a tacky or adhesive layer. The backing material is generally a strong, thin, flexible and lightweight material. Attached to one or both sides of the backing material is an electrically conductive material which forms the conductive layer. The conductive layer generally covers all or a substantial portion of one or both sides of the electrode.

Attached to at least a first portion of the conductive layer, on one side of the tab electrode, is an adhesive layer. This first portion of the tab electrode connected to the adhesive layer is typically called the body of the electrode. The adhesive layer is used to connect the tab electrode to the patient. The adhesive layer is electrically conductive and it establishes an electrical connection between the patient and the electrode. The adhesive layer is typically constructed of a tacky, electrically conductive gel.

The second or other portion of the electrode, which is not covered by the adhesive layer, is the tab portion of the electrode. The tab extends from the body of the electrode, which contains the adhesive layer, and is electrically conducting because of the conductive layer. This projecting tab is typically connected to the lead wire of the electrical equipment by an attachment such as a clasp or clip. Thus, an electrically conductive path is established between the patient the electrical equipment.

The use of a snap or tab electrode depends upon the type of cardiovascular monitoring to be conducted. For example, cardiovascular monitoring of a patient may be used in resting diagnostic procedures, surgical and emergency room procedures, intensive and critical care units, ambulatory monitoring, and stress diagnostic procedures. Accordingly, the time involved to conduct this cardiovascular monitoring varies because a simple EKG test to obtain a single tracing for diagnostic purposes may be carried out in a few minutes in a physician's office. Conversely, longer term monitoring applications, such as in critical or intensive care units, require that the electrodes remain attached to a patient's skin for a considerably extended period of time. Thus, the period of evaluation and the condition of the evaluation environment can differ widely among the various types of EKG procedures.

When cardiovascular monitoring of a patient is desired for an extended period of time, snap electrodes are typically used to connect the patient to the monitoring equipment because a long term connection between the patient and the EKG apparatus can be established. Snap electrodes can be attached to the patient's skin for up to three days, or sometimes longer, before replacement is required. During this extended time period, however, it is frequently desired to conduct other or more extensive monitoring or testing of the cardiovascular system of the patient. This additional testing often requires disconnection of the existing monitoring system and connection of the patient to a different apparatus. Because the additional testing often requires the use of electrodes placed at or near the same location as the existing electrodes, the connection or the existing electrodes themselves must be removed. For example, the new monitoring system can be connected to one or more of the female couplings of the existing snap electrodes. However, it is often preferred to remove the existing snap electrodes and connect new tab electrodes to the patient. Tab electrodes are used because they can be easily attached and removed from the patient.

The disconnecting of the female coupling from the snap electrode or replacement of the snap electrode with the tab electrode is laborious and takes an unnecessary amount of valuable time from the health care provider. This time and effort is magnified because this additional testing is often required two or three times per day. Additionally, when the lead wire to the EKG apparatus is disconnected or the snap electrode is removed from the patient, the EKG unit receives no electrical signal or impulses from the patient and this causes an alarm to sound. The ringing alarm is very distracting and the EKG unit must be turned off, disconnected or reset to stop the alarm. After the additional testing is completed, the patient must then be reconnected to the first monitoring device and the machine must then be restarted and checked to ensure that the unit is functioning properly. The constant attaching and removing of the adhesive surfaces of the electrodes has the disadvantage of tending to irritate the patient's skin. Further, the removal of the electrode from the patient's skin generally compromises the adhesive surface of the electrode, so the electrode must be frequently replaced and this increases the cost of the cardiovascular monitoring.

As known in the art, the placement of electrodes in a side-by-side arrangement is disadvantageous because that does not facilitate the accurate placement of either electrode. This may result in erroneous readings of the testing equipment.

It should be understood that the electrodes described herein are by way of example only, and medical electrodes having different constructions and designs may be used in accordance with the invention. There are many possible medical electrodes which may be used with the present invention. For example, medical electrodes having additional or fewer layers formed from different materials may be used without departing from the scope of the invention.

SUMMARY OF THE INVENTION

A need therefore exists for a medical electrode to which primary and auxiliary electrical instruments can be simultaneously attached so as to detect physiological electrical potentials at a specific location on a patient's body.

In accordance with one aspect of the present invention, a medical electrode includes an electrically conductive layer having proximal and distal portions. An aperture extends through the electrically conductive layer in the proximal portion. A tab portion of the electrode is formed on the distal portion of the electrically conducting layer.

Another aspect of the present invention involves a medical tab electrode for use with a snap electrode of the type having an electrically conductive post for connection to an electrical instrument. The tab electrode includes a support layer and an electrically conductive layer attached to the support layer. A conductive adhesive layer covers at least a portion of the conductive layer. An aperture is oriented to extend through the conductive adhesive layer, the conductive layer and the support layer. The aperture is sized to receive a portion of the snap electrode.

In accordance with additional aspects of the present invention, a medical electrode is provided for simultaneous use with a primary electrical instrument and an auxiliary electrical instrument. The medical electrode includes an electrically conductive base which supports and electrically conductive post. The post includes an engagement end, which is distal of the base. An electrically conductive tab of the medical electrode connects to the post.

In accordance with a method of electrically connecting at least one auxiliary electrical instrument to a snap electrode, a snap electrode of the type having an electrically conductive post for connection to a primary electrical instrument is provided. A tab electrode, which includes an electrically conductive layer in an aperture extending therethrough also is provided. The aperture is sized to receive the post of the snap electrode. The post is advanced through the aperture to establish an electrical connection between the post and the electrically conductive layer. A primary electrical instrument is attached to the post, and an auxiliary electrical instrument is attached to the conductive layer of the tab electrode.

BRIEF DESCRIPTION OF THE DRAWINGS

These and other features of the invention will now be described with reference to the drawings of preferred embodiments which are intended to illustrate and not to limit the invention, and in which:

FIG. 1 is a top plan view of a medical electrode in accordance with a preferred embodiment of the present invention;

FIG. 2 a side cross-sectional view of the medical electrode shown in FIG. 1 taken along lines 2—2;

FIG. 3 is a bottom plan view of the medical electrode shown in FIG. 1;

FIG. 4 is a top plan view of a plurality of medical electrodes of the type shown in FIG. 1;

FIG. 10 is a side elevational view of the medical electrode of FIG. 9 schematically illustrated as connected with the associated EKG clip and female electrical coupling; and FIG. 11 ms an enlarged side sectional view of a contact tab of the electrode within the area 11 of FIG. 10.

DETAILED DESCRIPTION OF PREFERRED EMBODIMENTS

Figure 7:
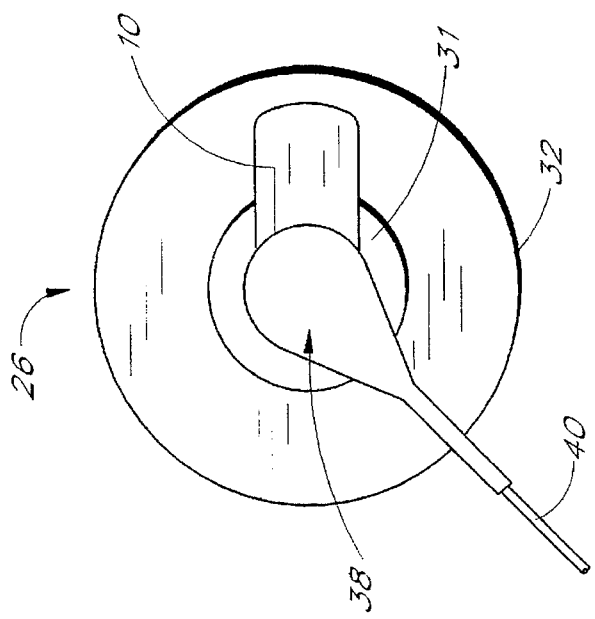
FIG. 7 is a top plan view of an assembly between the medical electrode, the snap electrode and a female coupling.

FIGS. 1–3 illustrates a medical electrode 10 configured in accordance with a preferred embodiment of the present invention. In the illustrated embodiment, the medical electrode 10 includes a backing layer 12, a conductive layer 14, an adhesive conductive layer 16, and an aperture 18.

The backing layer 12 of the medical electrode 10 is frequently constructed from a layer of generally flexible material such as polyethylene, polyvinyl polyester, or a mylar film. These materials allow the backing layer 12 to be light-weight, flexible and resilient. Those skilled in the art will appreciate the extensive list of materials which may be used to form the backing layer, and the backing layer 12 can be somewhat rigid.

The backing layer 12 can be perforated, solid and vapor impermeable, or solid and vapor permeable, as desired, in view of the intended application. The backing layer 12 is preferably stamped or cut from either sheet stock or ribbon stock. In one embodiment, the backing layer 12 comprises a mylar film having a thickness of about 0.002 to about 0.004 inches.

The conductive layer 14, which is a metal or foil layer, preferably lines the bottom surface of the backing layer 12, as shown in FIG. 2. The conductive layer 14 desirably spans the entire lower surface of the electrode 10. Although not illustrated, the conductive layer 14 also may be located on the upper surface of the backing layer 12. A metal such as tin or silver/silver chloride or another conductive material such as carbon, for example, may be used to form the conductive layer 14.

The conductive layer 14 can be formed separately from the backing layer 12, such as in the case of foil or conductive polymeric layers, and then adhered to the backing layer through any of a variety of techniques known in the art. Alternatively, the conductive layer 14 can be applied to the backing layer 12 such as by painting, spraying, vapor deposition, or other known techniques for applying a conductive film. As a further alternative, the functions of the backing layer 12 and conductive layer 14 are accomplished by a single electrically conductive support layer (not illustrated) formed of a conductive material (e.g., carbon), as will be understood by one of skill in the art in view of the disclosure herein.

The conductive layer 14 includes a proximal portion 19 and a distal portion 21. As used herein, the terms "proximal" and "distal" are used in reference to the conductive post 30 of the snap electrode (see FIG. 5) when the medical electrode 10 is attached to the conventional snap electrode 26, as discussed in detail below.

The adhesive conductive layer 16 is attached to the proximal portion 19 of the conductive layer 14, on the bottom surface of the electrode 10. The adhesive conductive layer 16 generally includes a tacky or adhesive gel that is used to hold the electrode 10 to a conventional snap electrode as described below. This gel layer may include any of a variety of known electrolytic gel materials which are electrically conductive and compatible with the conductive layer 14. This conductive layer 14, for example, may be constructed of materials such as a silver/silver chloride, metal foil or laminate, or a non-woven web impregnated with a conductive material. A variety of conductive adhesives are known to those skilled in the art, and any of these can be utilized to provide electrical interface between the electrode 10 and the snap electrode.

The distal portion 21 of the electrode 10, which does not necessarily contain the adhesive conductive layer 16, forms the tab 20. The tab 20 extends outwardly from the body 22 of the electrode 10 and is electrically conductive because of the conductive layer 14. This tab 20 is specifically adapted to provide an electrical connection between the wire lead from an EKG unit, or other electrical instrumentation, and the electrode body 22 attached either directly to the patient's body or to a conventional snap electrode. The tab 20 may take the form of a flat strip, wire, or other configuration, depending upon the intended use environment.

In the illustrated embodiment, the tab electrode 10 is approximately 1.125 inches (2.9 cm) in length and about 0.5 inch (1.3 cm) in width. The adhesive conductive layer 16 extends between about 0.5 inch (1.3 cm) and 1.0 inch (2.54 cm) from one side of the electrode 10. Most preferably, the adhesive conductive layer 16 extends about 0.75 inch (1.9 cm) to substantially cover the body 22 of the electrode 10. The dimensions and the shape of the medical electrode 10, however, can readily be customized to suit specific applications.

As seen in FIG. 4, the tab electrodes 10 of the present invention may be manufactured in batch lots such that, when first manufactured, a protective release layer or non-stick backing sheet 24 is secured to the adhesive conductive layer 16 of the electrode 10. The backing sheet 24 can be selectively separated from the conductive adhesive layer 16 to expose the conductive adhesive surface of the electrode so the electrode 10 can be attached to a snap electrode 26 or skin of a patient. As known in the art, a variety of materials may be used for the release layer. Alternatively, the electrode 10 could exist separately with individual release layers.

As seen in FIGS. 1 and 3, the body 22 of the tab electrode 10 defines the aperture 18. The aperture 18 has a diameter which is specifically sized and configured to engage an electrically conductive post 27 of a snap electrode 26 (see FIG. 5). In the illustrated embodiment the diameter of the aperture 18 equals about 0.3 inch (0.8 cm). As will be readily understood and appreciated, however, the size of the aperture 18 and the dimensions of the electrode 10 can be varied according to the dimensions of the snap electrode 26.

The application of the medical electrode 10 with a conventional snap electrode 26 will now be described in connection with FIGS. 5 through 8. These figures illustrate a representative snap electrode 26 for exemplary purposes. As a basic understanding of the snap electrode 26 is essential to an appreciation of the application of the present medical electrode 10, the following will first describe the snap electrode 26 before addressing the application of the present electrode 10 with the snap electrode 26.

Figure 8:
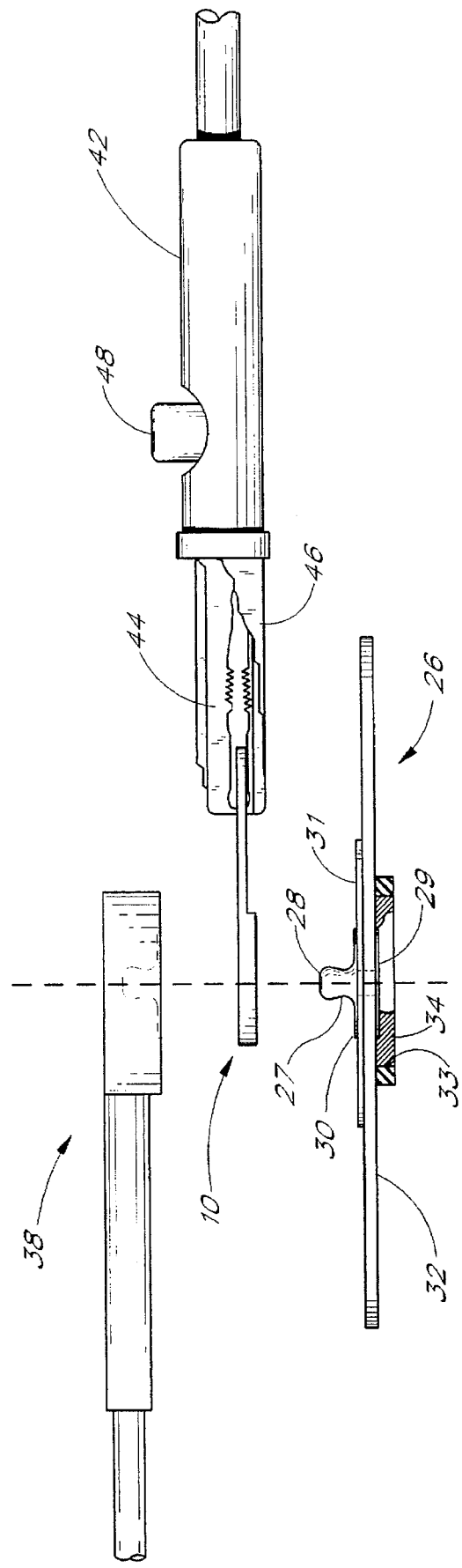
FIG. 8 is an exploded side elevational view of an assembly of the medical electrode, snap electrode and female coupling, together with a clip attached to a tab portion of the medical electrode.

As best understood from FIG. 8, the snap electrode 26 includes an electrically conductive post 27 with an outer engagement end 28. The exemplary snap electrode 26 illustrated in FIG. 8 includes a ball stud as the engagement end 28; it should be understood, however, that the present electrode 10 can be used with other stationary electrodes which have any of a variety of other types of connectors, such as, for example, clips, snaps, sockets, banana plugs, female couplings, direct attachment of electrically conducting wires, and the like. The post 27 and the ball stud 28 preferably are constructed of stainless steel, but any of a wide variety of conductive materials also can be used.

A base 29 supports the post 27 at an end of the post 27 opposite of the ball stud 28. The post 27 also supports a contact 30, which is suspended above the base 29. As best understood from FIG. 5, the contact 30 and the base 29 desirably have circular shapes of generally the same size. As such, the base 29 and the contact 30 each have a disk-like shape arranged parallel to each other with the post 27 extending generally perpendicular to the base 29 and to the contact 30. The base 29, post 27 and contact 30 are all in electrical contact with one another.

Figure 5:
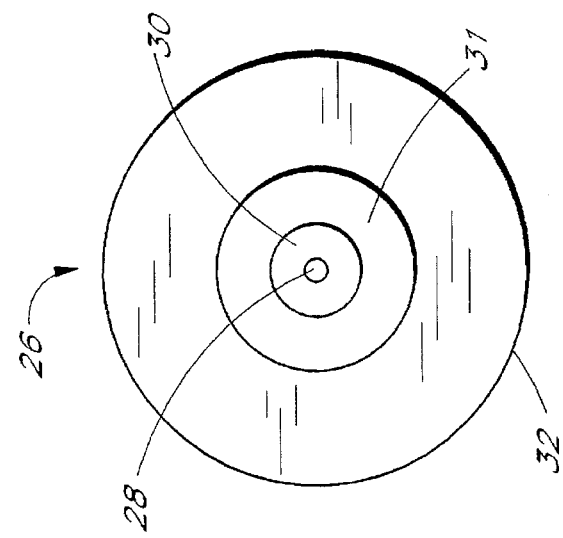
FIG. 5 is a top plan view of a conventional snap electrode.

As seen in FIGS. 5 and 8, an adhesive pad 32 of the snap electrode 26 anchors the base 29 and the conductive post 27 to the patient's tissue. The adhesive pad 32 commonly includes a cellulose foam layer and a bottom adhesive layer. The adhesive bottom surface is attached to the patient's tissue (e.g., skin) when used, as known in the art. The base 29 and the contact 30 are arranged so as to interpose the adhesive pad 32 between the base 29 and the contact 30.

A lead stabilizer or insulating member 31 is often interposed between the base 29 and the contact 30, usually between the contact 30 and the upper surface of the adhesive pad 32. The lead stabilizer 31 typically is a plastic or paper disk which has a diameter larger than the base 29 and the contact 30. The lead stabilizer 31 is preferably constructed from a non-electrically conducting material to limit undesirable electrical contact or interference with the electrode 10. It is known, however, that many snap electrodes 26 do not contain a lead stabilizer 31.

As seen in FIG. 8, the adhesive pad 32 defines a receptacle 33 which receives the base 29 with the conductive post 27 extending through the foam layer of the pad 32 and through the lead stabilizer 31. The ball stud 28 extends above the adhesive pad 32 for connection with an electrical-female-snap connector 38, as discussed below. A conductive material 34 fills the receptacle 33 of the adhesive pad 32. The conductive material 34 typically is either an electrically conductive gel or a porous foam impregnated with a conductive material, as known in the art. The conductive material 34 establishes an electrical connection between the patient's tissue (e.g., skin) and the base 29 of the conductive post 27.

Figure 6:
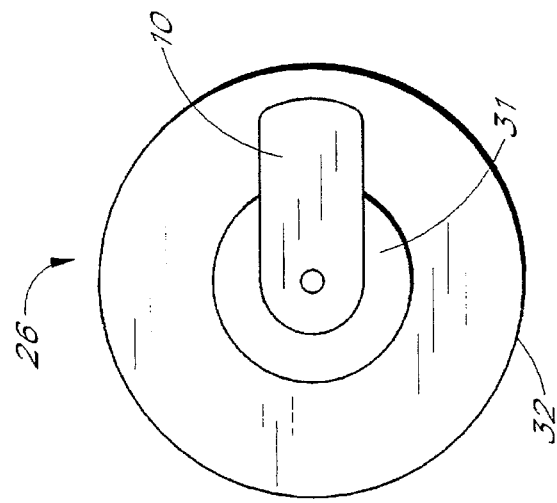
FIG. 6 is a top plan view of the medical electrode of FIG. 1 attached to the conventional snap electrode.

As best seen in FIGS. 6 and 8, the present medical electrode 10 is electrically connected to the snap electrode 26 by inserting the ball stud 28 through the aperture 18 and engaging adhesive conductive layer 16 with the post 27 and contact 30. The adhesive connection between the adhesive layer 16 and the contact 30, and the physical connection between the post 27 and the aperture 18 secures the present medical electrode 10 to the snap electrode 26 and establishes an electrical interconnection between the snap electrode 26 and the medical electrode 10. As seen in FIG. 7, the tab electrode 10 does not interface with the attachment of the female coupling 38 and wire 40 of a primary electrical instrument to the snap electrode 26. Further, as seen in FIG. 8, electrical interconnection can be made to the medical electrode 10 by a conventional alligator clip 42 or other conventional connector while the female coupling 38 remains attached to the snap electrode 26. The female coupling 38 may include a variety electrical connections to the ball stud 28, including, for instance, snaps, clips, direct connection of electrical wires, and the like.

The clip 42 desirably comprises an "alligator" type clip having a pair of opposing jaws 44, 46. The jaws 44, 46 are electrically conductive and specifically adapted to engage the electrode 10. The jaws 44, 46 establish an electrical connection between the electrode 10 and the clip 42. As known, the clip 42 normally connects to an electrically conductive wire which then can be connected to the monitoring equipment, typically auxiliary electrical instrumentation, such as an EKG cart.

The movement of the jaws 44, 46 of the clip 42 is controlled by a button 48. The jaws 44, 46 are normally biased in a closed position by a spring (not shown). The button 48 is pushed to open the jaws 44, 46 of the clip. This allows the electrode 10 to be inserted between the jaws 44 and 46. Release of the button 48 closes the clip 42 with the jaws 44, 46 to clamp onto the tab portion 20 of the electrode 10.

As seen in FIGS. 6–8, two electrical paths are simultaneously established when the electrode 10 is attached to the snap electrode 26. A first electrical path exists between the electrically conduction material 34, the base 29, the conductive post 27, and the female coupling 38. A second path exists between the electrically conducting material 34, the base 29, the conductive post 27, the contact 30, and the electrode 10. Thus, an electrical connection can be established between a patient and two electrical monitoring or testing devices.

It also should be understood that the present medical electrode 10 can be used independent of a conventional snap electrode 26. In this use, the medical electrode 10 is attached directly to the tissue of the patient (e.g., directly to the patient's skin) and connected to a medical-electrical instrument for monitoring or testing purposes, as known in the art.

In this manner, one type of electrode may be used either in combination with an existing electrode, such as a snap electrode, or as a conventional tab electrode, depending upon the specific application of the electrode 10.

Figure 9:
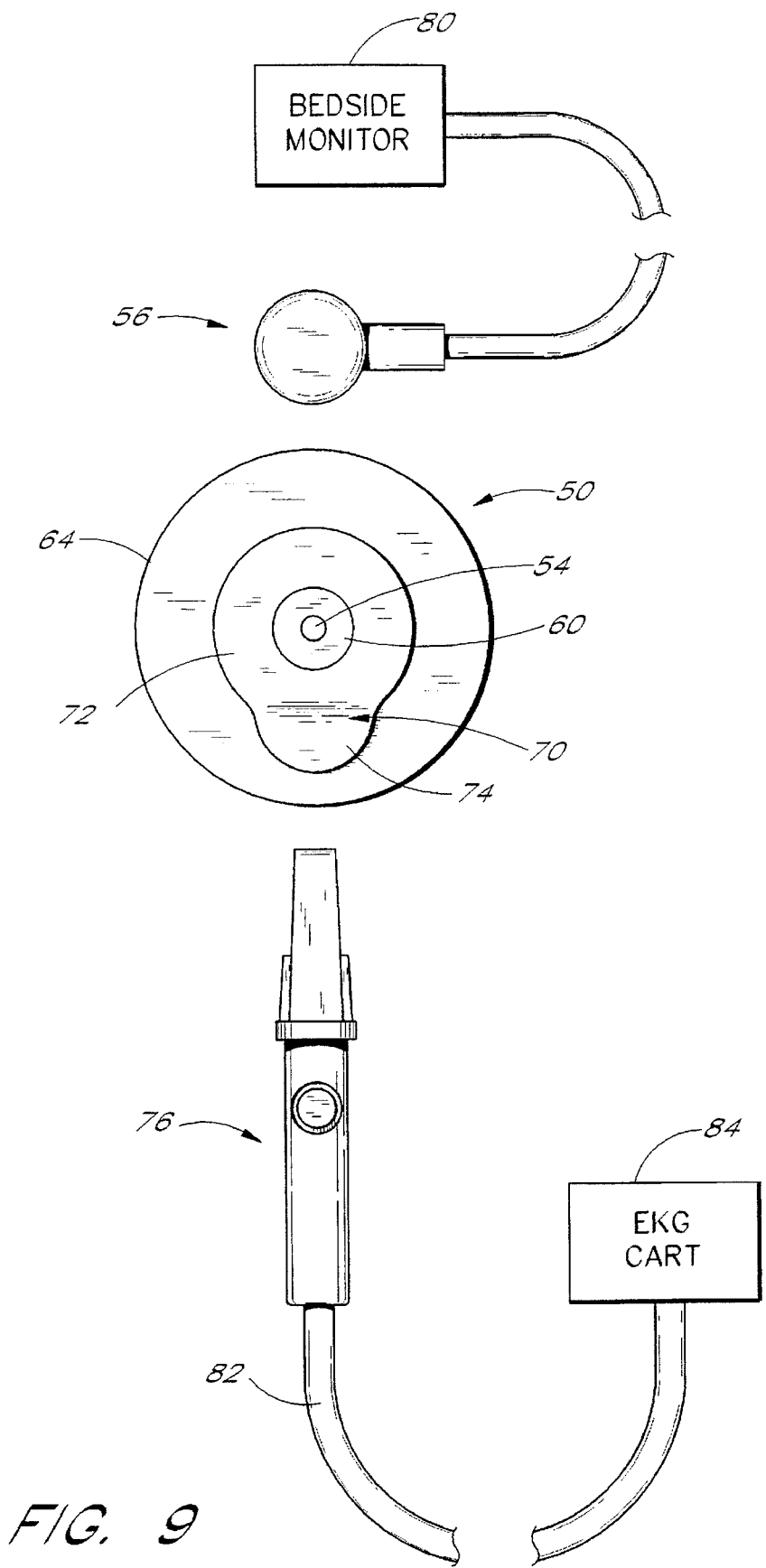
FIG. 9 is a top plan view of a medical electrode in accordance with another preferred embodiment of the present invention, illustrated with an associated EKG clip and a female electrical coupling.

FIGS. 9 through 11 illustrate a medical electrode 50 which is configured in accordance with another preferred embodiment of the present invention. The medical electrode 50 includes an electrically conductive post 52 with an outer engagement end 54 which is configured to engage a corresponding electrical connector 56 of a medical-electrical instrument for monitoring or testing purposes. In the illustrated embodiment, the engagement end 54 is configured as a ball stud designed to engage a corresponding electrical-female-snap connector. It should be understood, however, that the present electrode 50 can include an engagement end 54 which is configured to engage any of a variety of other types of electrical connectors 56, such as, for example, pre-attached lead wires, banana plugs, sockets, clips, snaps and pre-attached female sockets. The conductive post 52 and the ball stud 54 preferably are constructed of stainless steel, but any of a wide variety of conductive materials also can be used.

As best understood from FIG. 10, a base 58 supports the conductive post 52 at an end of the post 52 opposite of the ball stud 54. The post also supports a contact 60, which is suspended on the post 52 above the base 58. The contact 60 and the base 58 desirably have a circular disc-like shapes of generally the same size. The base 58 and the contact 60 desirably are arranged parallel to each other with the conductive post 52 extending generally perpendicular to the base 58 and the contact 60. The base 58, conductive post 52 and the contact 60 desirably are integrally formed with one another and are constructed of stainless steel; but again, any of a wide variety of conducting materials also can be used. As such, the base 58, the conductive post 52, and the contact 60 are all in electrical connection with one another.

As seen in FIG. 10, an insulating member 62 may be interposed between the base 58 and the contact 60. The insulator member 62 desirably is a plastic or paper disc which has a diameter larger than the base 58 or the contact 60. The insulator member 62, however, can be formed of any of a wide variety of non-conductive materials. Additionally, the electrode 50 can be configured without the insulating member 62 equally as well.

The medical electrode 50 also includes an adhesive pad 64 which is used to anchor the base 58 and the conductive post 52 to the patient's tissue (e.g., skin). The adhesive pad 64 desirably includes a layer of cellulose foam or other elastic material, with a bottom adhesive surface. The adhesive pad 64 may also include other laminate layers, such as an upper paper or non-woven cloth layer, to suit specific applications as will be readily apparent to those skilled in the art. The thickness of the foam layer of the adhesive pad 64 also may vary to suit specific applications; however, the adhesive pad 64 desirably has a sufficient thickness so as to provide some degree of cushion to absorb the connection force between the electrical connector 56 and the engagement end 54 of the conductive post 52, as well as to support the base 58 and conductive post 52 of the electrode 50. The adhesive bottom surface of the pad 64 is attached to the patient's tissue (e.g., skin) when used, as known in the art.

A removable paper or plastic release layer (not shown) desirably covers the bottom adhesive layer of the adhesive pad 64 before use. The release layer desirably extends beyond the edges of the adhesive pad 64 to ease removal of the pad 64 from the release layer.

In the illustrated embodiment seen in FIG. 10, the base 58 is generally coterminous with the adhesive layer of the adhesive pad 64, and the conductive post 52 extends through the foam layer of the pad 64 and through the insulator member 62. The base 58 and the contact 60 are arranged so as to interpose the adhesive pad 64 and the insulator member 62 between the base 58 and the contact 60. The engagement end 54 of the conductive post 52 extends above the adhesive pad 64 for connection with the electrical connector 56, as discussed below.

As also seen in FIG. 10, a conductive material 68 is positioned on the adhesive surface of the adhesive pad 64. The conductive material 68 desirably is an electrically conductive gel or a porous foam impregnated with a conductive material. In the illustrated embodiment, the conductive material 68 is a patch of electrically conductive gel that covers at least a portion of the base 58. A variety of conductive materials which are known to those skilled in the art, however, may also be used to provide electrical interface between the electrode 50 and the patient. The conductive material 68 thus establishes an electrical connection between the patient's tissue (e.g., skin) and the base 58 of the conductive post 52.

The electrode 50 also includes a tab contact 70 which is electrically connected to the contact 60 on the post 52. The tab contact 70 is interposed between the contact 60 and the base 58 and, in the illustrated embodiment, the tab contact 70 is interposed between the contact 60 and the insulating member 62. It should be understood, however, that the tab contact 70 electrode 50 could be positioned above the contact 60.

The tab contact 70 includes a body 72 and a tab portion 74. The body 72 desirably is firmly attached to the contact 60 and the tab portion 74 extends from the body 72 to lie loosely above the adhesive pad 64 and away from the contact 60. As seen in FIG. 10, the tab portion desirably bends upwardly away from the adhesive pad 64 to facilitate attachment of an electrical clip 76, as discussed below.

As best understood from FIG. 11, the tab contact 70 desirably has a laminate structure formed in part by a conductive layer 78. The conductive layer desirably is a metal or foil layer, such as, for example, tin or silver/silver chloride. Those skilled in the art, however, will readily appreciate that any of a wide variety of conductive materials can be used to form the conductive layer 78. For instance, rather than a laminate structure, the tab contact 70 can be formed as a layer of conductive carbon film equally as well.

In the illustrated embodiment, the conductive layer 78 can be formed independently of a substrate, such as in the case of foil or conductive polymeric layers or can be attached to a supporting substrate. In the latter case, as illustrated in FIG. 11, the conductive layer 78 can be adhered to a substrate 79 through any of a variety of known techniques or in the alternative the conductive layer 78 can be applied to the substrate by such techniques as painting, spraying, vapor deposits, or other known techniques for applying a conductive film.

The tab contact 70 desirably also includes an adhesive conductive layer 80 on the bottom side of the portion of the conductive layer 78 that forms the body 72 of the contact tab 70. The adhesive conductive layer 80 desirably is a tacky or adhesive gel and the adhesive conductive layer 80 may include any of a variety of known electrolytic gel materials which are electrically conductive and compatible with the conductive layer 78. In the illustrated embodiment in which the conductive layer 78 is formed of a silver/silver chloride, metal foil or laminate, it is understood that a variety of conductive adhesives which are well known to those skilled in the art, such as, Promion™, manufactured by Promion, Inc., can be used to provide an electrical interface between the conductive layer 78 and the contact 60.

With reference to FIG. 10, the tab portion 74 of the contact tab 70 extends outwardly from the body 72 and is electrically conductive because of the continuous conductive path formed by the conductive layer which integrally extends between the body 72 and the tab portion 74 of the tab contact 70. The tab portion 74 is specifically adapted to provide an electrical connection between the wire lead from an EKG unit or other electrical instrumentation, and the electrode 50 which is attached to the patient's body. In the illustrated embodiment, the tab portion 74 has a flat strip-like shape; however, the tab portion 74 may take the form of a wire, or other configuration, depending upon the intended use environment.

The tab contact 70 alternatively can be a conductive layer that is either formed independently of a substrate or attached to a supporting substrate. The tab contact 70 is interposed between the contact 60 and the adhesive pad 64 such that the tab contact 70 is securely held between the contact 60 and the adhesive pad 64. The electrically conducting surface of the contact 70 is positioned in electrical engagement with the contact 60 to create an electrical path between the tab contact 70 and the contact 60. Thus, an adhesive conductive layer is not required to secure the tab contact 70 between the contact 60 and the adhesive pad 64.

As understood from FIGS. 9 and 10, the present medical electrode 50 can be simultaneously connected to two different pieces of electrical equipment. The electrode 50 is initially attached to the patient at a desired location on the patient's body, such as, for example, connected to the chest of the patient proximate to the patient's heart. The act of attaching the electrode 50 to the patient involves removing the release layer from the back of the adhesive pad 64 and pressing the adhesive pad 64 firmly against the patient's skin so as to cause the conductive material 68 within the recess 66 of the pad 64 to contact the patient's skin. The adhesive layer of the pad 64 prevents the electrode 50 from migrating or easily detaching from the patient's tissue.

In the illustrated embodiment, the electrical connector 56 can be a female snap connector which is connected to the ball stud 54 of the medical electrode 50. It will be understood that the electrical connector 56 can include a variety of connections including clips, sockets, banana plugs, direct attachment of electrically conducting wires and the like. The female coupling 56 may be connected by an electrical wire 81 to a wide variety of electrical components, such as a bedside monitor 83, to measure the cardiovascular activity of the patient. The tab portion 74 of the tab contact 70 preferably is connected by the clip or clasp 76 to an electrical component. The clip 76 preferably comprises a conventional "alligator" type clip. The clip 76 may be connected by a wire 82 to various electrical equipment 84, such as an EKG cart.

As common to the above-described embodiments, the medical electrode of the present invention allows for the simultaneous attachment of electrical connectors which communicate with primary and auxiliary medical-electrical instruments. As such, at least two different electrical instruments may detect physiological electrical potentials at a specific location at the same time without the need to exchange electrodes or to disconnect preexisting monitoring or testing equipment.

Although this invention has been described in terms of certain preferred embodiments, other embodiments apparent to those of ordinary skill in the art are also within the scope of this invention. Accordingly, the scope of the invention is intended to be defined only by the claims which follow.

What is claimed is:

1. A medical electrode for simultaneous use with a primary electrical instrument and an auxiliary electrical instrument, said medical electrode comprising an electrically-conductive base supporting an electrically-conductive post, said post including an engagement end distal of said base, an electrically-conductive tab coupled to said post, and an adhesive pad including an adhesive surface intended to adhere to a patient's skin, said tab being positioned on a side of said adhesive pad opposite of the adhesive surface to separate said tab from the patient's skin.

2. A medical electrode as in claim 1 additionally comprising a contact supported by and in electrical contact with said post, said contact electrically connected to said conductive tab.

3. A medical electrode as in claim 1, wherein said engagement end comprises a ball stud configured to engage a corresponding electrical, female-snap connector.

4. A medical electrode as in claim 1, wherein said conductive tab comprises an electrically conductive layer having a tab portion and a contact portion which extends from said tab portion and electrically connects with said post to established an electrical connection between said tab portion and said post.

5. A medical electrode as in claim 4, wherein said tab portion is configured so as to allow attachment of an electrical clip of the auxiliary electrical instrument.

6. The electrode of claim 4, wherein said conductive tab additionally comprises a support layer to which at least a portion of the conductive layer is attached, a conductive adhesive layer on at least a portion of said conductive layer, and an aperture which extends through at least one of said conductive and support layers.

7. A medical electrode as in claim 4, wherein said tab portion is electrically coupled to said base.

8. A medical electrode as in claim 7, wherein an electrically-conductive, adhesive material is positioned between said base and said tab portion.

9. A medical electrode as in claim 4, wherein said tab portion is electrically coupled to said post.

10. A medical electrode as in claim 1 additionally comprising an electrically-conductive material contacting at least a side of said base which is opposed to the side to which said post is connected.

11. A medical electrode as in claim 10, wherein said electrically-conductive material is a gel.

12. A medical electrode as in claim 10, wherein said electrically-conductive material has a larger skin contact area than a corresponding area of the base.

13. A medical electrode as in claim 1, wherein an electrically conductive material covers a portion of a side of said tab which juxtaposes said adhesive pad to place said tab in electrical communication with the patient's skin with the adhesive pad secured to the patient.

14. A medical electrode system comprising an electrically-conductive base element adapted to contact the skin of a patient, an electrically-conductive tab electrically coupled to said base element, and an adhesive pad intended to adhere to the patient's skin while supporting said tab above and separating said tab from the patient patient's skin, said base element electrically communicating with a first electrical wire for connection to a first electrical instrument, said base element also electrically communicating with a second electrical wire for connection to a second electrical instrument, said second wire being electrically coupled to said tab.

15. The electrode system of claim 14, wherein said base element includes an electrically-conductive post which engages a connector on an end of said first electrical wire.

16. The electrode system of claim 15, wherein said post includes an outer engagement end.

17. The electrode system of claim 16, wherein said engagement end includes a ball stud configured to engage a female snap connector.

18. The electrode system of claim 17, wherein said base element comprises an electrically-conductive base covered by an electrically-conductive adhesive layer.

19. The electrode system of claim 18, wherein said tab is positioned between said base and said engagement end of said post.

20. The electrode system of claim 19, wherein said tab comprises an electrically-conductive layer, a nonconductive support layer adjacent a first side of said electrically-conductive layer, and an adhesive layer on at least a portion of a second side of said electrically-conductive layer.

21. The electrode system of claim 20, wherein said support layer and said conductive layer have proximal and distal ends, said distal ends of said support and conductive layers forming a tab portion of said tab electrode.

22. The electrode system of claim 14, wherein said adhesive pad comprises a first layer adjacent to said tab and an adhesive layer, and said adhesive pad is larger than said tab.

23. The electrode system of claim 14, wherein said base element comprises an electrically-conductive base covered by an electrically-conductive adhesive layer.

24. A medical electrode as in claim 23, wherein said electrically-conductive adhesive layer is a layer of electrically-conductive gel.

25. The electrode system of claim 23, wherein said electrically-conductive adhesive layer is a porous foam layer impregnated with an electrically-conductive substance.

26. A method of electrically connecting at least one auxiliary electrical instrument to a snap electrode, comprising the steps of:

providing a snap electrode of the type having an electrically-conductive post for connection to a primary electrical instrument, said post connected to a nonconductive adhesive pad;

providing a tab electrode of the type having an electrically-conductive layer and an aperture extending therethrough, said aperture sized to receive said post;

advancing the post through the aperture to establish an electrical connection between the post and the electrically-conductive layer and wherein said adhesive pad supports said tab electrode;

connecting a primary electrical instrument to the post; and connecting an auxiliary electrical instrument to the electrically-conductive layer.

27. A method of electrically connecting at least one auxiliary electrical instrument to a snap electrode, comprising the steps of:

providing a snap electrode of the type including both an electrically-conductive post and a tab electrode, the tab electrode having an electrically-conductive layer in electrical communication with said post;

connecting a primary electrical instrument to the post; and connecting an auxiliary electrical instrument to the electrically-conductive layer.

* * * * *

UNITED STATES PATENT AND TRADEMARK OFFICE
CERTIFICATE OF CORRECTION

PATENT NO. : 5,626,135
DATED : May 6, 1997
INVENTOR(S) : Sanfilippo, Robert M.

It is certified that error appears in the above-indentified patent and that said Letters Patent is hereby corrected as shown below:

In column 4, line 19, "2 a side" should be --2 is a side--.

In column 4, line 43, "11 ms an" should be --11 is an--.

In column 9, line 29, "that the tab contact 70 electrode 50" should be --that the tab contact 70--.

In Claim 14, column 11, line 54, "the patient patient's skin" should be --the patient's skin--.

In Claim 21, column 12, line 20, "said tab electrode." should be --said tab.--.

Signed and Sealed this

Twenty-fifth Day of November, 1997

*Attest:*

BRUCE LEHMAN

*Attesting Officer*     *Commissioner of Patents and Trademarks*